United States Patent [19]

Liang et al.

[11] Patent Number: 5,012,797
[45] Date of Patent: May 7, 1991

[54] METHOD FOR REMOVING SKIN WRINKLES

[75] Inventors: Marc D. Liang; Krishna Narayanan, both of Pittsburgh, Pa.

[73] Assignee: Montefiore Hospital Association of Western Pennsylvania, Pittsburgh, Pa.

[21] Appl. No.: 461,624

[22] Filed: Jan. 8, 1990

[51] Int. Cl.$^5$ .............................................. A61B 17/32
[52] U.S. Cl. .................................... 128/24 A; 604/22; 606/131
[58] Field of Search .................... 128/24 A, 897, 898; 606/131, 132; 604/22

[56] References Cited

U.S. PATENT DOCUMENTS

| | | | |
|---|---|---|---|
| 3,526,219 | 9/1970 | Balamuth | 128/24 A |
| 3,608,553 | 9/1971 | Balamuth | 606/131 |
| 3,990,452 | 11/1976 | Murry et al. | 128/24 A |
| 4,040,414 | 5/1976 | Suroff | 128/24 A |
| 4,874,361 | 10/1989 | Liang et al. | 128/395 |

OTHER PUBLICATIONS

Harrison's Principles of Internal Medicine, 10th Edition, Petersdorf et al., McGraw-Hill, Inc., 1983, p. 835.
The Pharmacological Basis of Therapeutics, 4th Edition, Goodman et al., MacMillan Company, 1970, pp. 376, 388-389 and 997.

*Primary Examiner*—Lee S. Cohen
*Assistant Examiner*—K. M. Pfaffle
*Attorney, Agent, or Firm*—Harry B. Keck

[57] ABSTRACT

Mammal skin having wrinkles can be treated to remove wrinkles by abrading elevated portions of the epithelial layer with an ultrasonic surgical tool adapted to abrade soft tissue. The subcutaneous tissue in the selected region is medicated by subcutaneous injection of anaesthetic, vaso constrictor and spreading factor in effective quantities.

5 Claims, 1 Drawing Sheet

METHOD FOR REMOVING SKIN WRINKLES

BRIEF DESCRIPTION OF THE INVENTION

1. Field of the Invention

This invention relates to a method for removing skin wrinkles from a region of living mammal skin. More particularly the selected region of the mammal skin is pretreated subcutaneously with an anaesthetic, a vaso-constrictor and an enzyme spreading factor. The selected region thereafter is treated with an ultrasonic surgical tool having a high frequency oscillating tip.

2. Background of the Invention

Ultrasonic surgical tools are widely used in dental treatment and other surgical procedures such as cataract removal (U.S. Pat. No. 3,589,363), neuro-surgery (U.S. Pat. No. 4, 016,882).

U.S. Pat. No. 3,526,219 describes removing a discreet layer from an outer layer of tissue in human anatomy.

There are several ultrasonic surgical tools available. All such tools have a forward tip which oscillates co-linearly or transversely with respect to the longitudinal axis of the ultrasonic tool. Such ultrasonic surgical tools frequently are provided with an annular aspirating passageway to facilitate removal of fragmented tissue from the fragmentation site.

The ultrasonic surgical tools are commonly available to operate at 23 Hz or at 37Hz. Power output is available at 20 to 100 watts.

So far as can be determined, ultrasonic surgical tools have not been employed for treating skin. There are several reasons which might explain this failure of the surgical art to adopt ultrasonic surgical tools for skin treatment.

One reason is that the use of ultrasonic tools is locally painful to the patient. Another reason is that the skin treatment tends to create excessive localized bleeding. Another reason is that no appropriate circumstances for skin treatment have been identified.

STATEMENT OF THE INVENTION

According to the present invention, skin wrinkles can be removed from a selected region of the skin of a living mammal by using an ultrasonic surgical tool of the type described in U.S. Pat. Nos. 3,526,219, 4,016,882 and others. Such devices have a projecting oscillating hard tip which oscillates at ultransonic frequencies to cause fragmentation of living cells which come into contact with the oscillating tip. According to this invention, the region of the skin to be treated is injected subcutaneously with A. A local anaesthesic;
B. A vaso constrictor;
C. A spreading enzyme factor. The local anaesthesic reduces the localized pain for the patient. The vaso constrictor reduces the tendency of the treated area to bleed. The spreading enzyme factor promotes the uniform distribution of the anaesthesia and the vaso constrictor throughout the treatment area. With the skin area thus prepared, an operator can remove selected elevated portions of the epithelial layer in the selected skin region with little pain for the patient and with reduced localized bleeding. The subepithelial skin layers heal to form fresh scar tissue having reduced surface irregularities. Oscillatory frequencies of 20,000 Hertz to 50,000 Hertz are effective for the high frequency vibrating tool.

When the process is carried out at high power input levels, 35 to 50 watts (compared to 20 watts), the treated skin appears to heal in less time.

DESCRIPTION OF THE PREFERRED EMBODIMENTS

Figure 1:
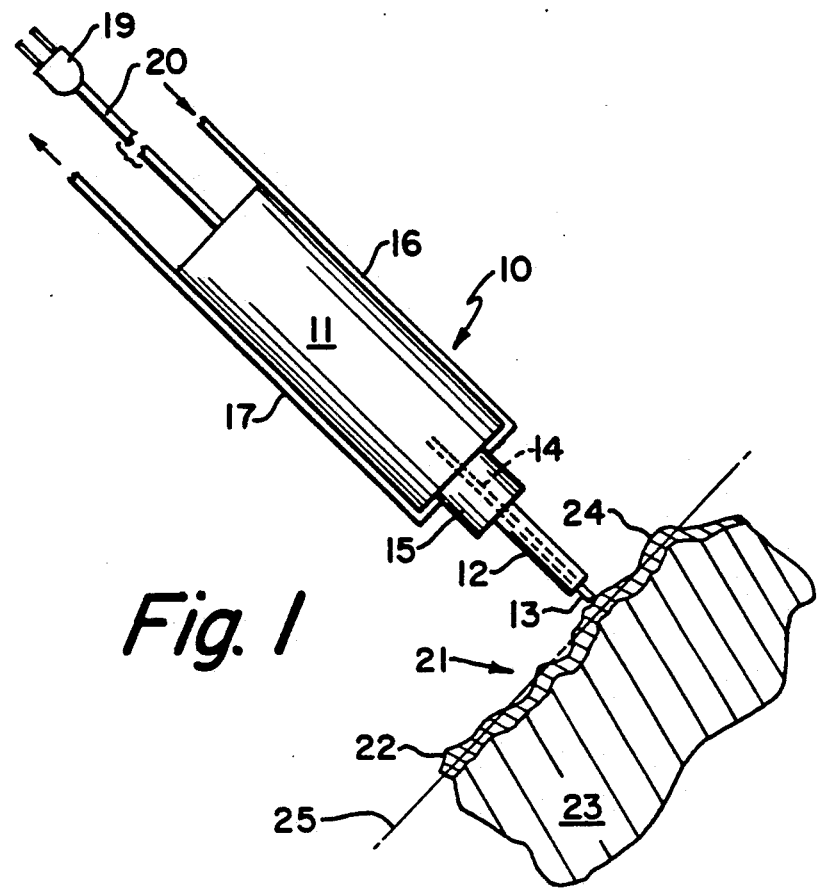
FIG. 1 is a side elevation of an ultrasonic surgical tool and a fragmentary cross-section of a region of wrinkled or scarred skin and subcutaneous tissue.

Ultrasonic surgical tools are well-known for fragmenting mammal tissue as a result of the vibratory forces generated at the oscillating tips of such devices. The vibratory intensity can be measured in peak-to-peak accelerations (U.S. Pat. No. 3,526,219) or in vibration frequency and vibratory amplitude (U.S. Pat. No. 4,016,882). Such tools have been commercially available from Cavitron Corporation. As shown in FIG. 1, an ultrasonic surgical tool 10 includes a hand-held body portion 11, a forwardly projecting pipe 12 with a forwardly projecting oscillatory tip 13. The oscillatory tip 13 is connected by a rod 14 which extends into a hand-held casing 11 and which receives oscillatory mechanical stress resulting in oscillatory movement of the tip 13. A manifold 15 is provided for receiving rinsing liquid from a conduit 16. The rinsing liquid is delivered, preferably as a mist, from the conduit 16 through the manifold 15 and in the annular space between the rod 14 and pipe 12 to the region of the oscillating tip 13. The rinsing liquid is aqueous saline solution. Suction means (not shown) may be provided to withdraw rinsing fluid, blood and tissue fragments upwardly through the annular space between the rod 14 and the pipe 12, through the manifold 15 and the suction conduit 17 for separate removal. A preferred tip 13 is a 2 mm diameter hollow tube. Alternatively the rod 14 may be solid rod with a diameter of about 2 mm at the tip 13. A source of electrical power is connected through a plug 19 and conductors 20 to drive the oscillatory generator within the hand-held casing 11. A region 21 of wrinkled skin 22 has subcutaneous tissues 23 which may be muscle, fat, or other mammal tissues.

Referring to FIG. 1, the operator prepares the subcutaneous tissue 23 by injecting subcutaneously through the skin 22 an effective amount of anaesthesic, an effective amount of vaso constrictor and an effective amount of an enzyme spreading factor. The injection is made a suitable time before the skin treatment commences in order for the anaesthetic, vaso constrictor and enzyme spreading factor to become effective. the subcutaneous injection is preferably made with a long needle parallel to the skin surface.

Figure 2:
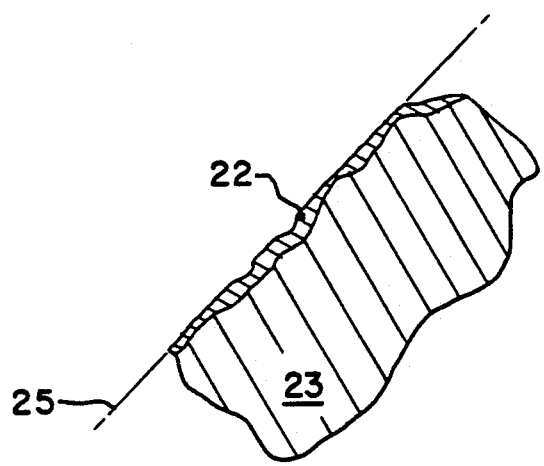
FIG. 2 shows the fragmentary cross-section of skin and subcutaneous tissue with a portion of the epithelial layer removed in accordance with this invention.

Then the operator directs the oscillating tip 13 over the selected portions of the epithelial layer 24 to those portions which are elevated above a normal surface of the skin 22, indicated by the line 25 in FIGS. 1 and 2. After the operator has completed the selective epithelial tissue abrasion, the skin region appears as shown in FIG. 2 with selected, elevated portions of the epithelial layer 24 being selectively abraded ro reduced in thickness in those portions which previously extended above the normal surface (indicated by the line 25). The subepithelial skin layer is in part exposed and is readily healed with fresh tissue. Either of the commercially available ultrasonic surgical tools is effective, i.e., 23,000 Hertz and 37,000 Hertz. Power output of 20 watts is effective. Higher power output of 35 to 50 watts appears to result in more rapid healing of the treated skin.

Figure 3:
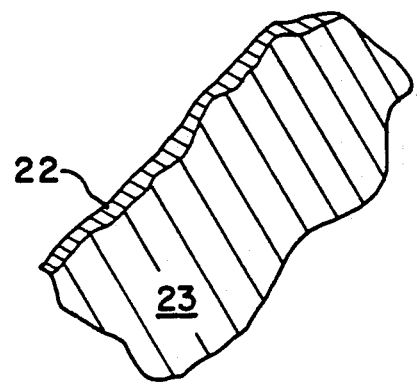
FIG. 3 is a fragmentary cross-sectional view of skin and subcutaneous tissue after the exposed skin tissue has healed.

After the skin 22 has healed, the freshly formed tissue, as shown in FIG. 3, tends to be relatively smooth and flat. The resulting skin, as shown in FIG. 3, has fewer wrinkles and skin surface irregularities are less apparent.

ANAESTHETIC

Lidocaine is a preferred local anaesthesic which presents few side reactions and few lingering effects yet is effective in reducing pain. Lidocaine customarily is provided with epinephrine solutions which have a low pH. Effective solutions of lidocaine contain about 1 ml lidocaine in 10,000 ml aqueous saline solution.

VASO CONSTRICTORS

Vaso constrictors function to contract blood vessels and retard the free release of blood in the affected region. Epinephrine is a preferred vaso constrictor. The epinephrine can be combined with the lidocaine solution in a single injection dose. The solution of epinephrine or other vaso constrictor preferably is about 1:200,000 (epinephrine: aqueous saline solution).

SPREADING FACTOR

A spreading factor functions to cause subcutaneous fluids to diffuse evenly throughout subcutaneous tissue. A preferred spreading factor is hyaluronidase. An appropriate dosage of the spreading factor is about three drops in an injection dose.

Combinations of anaesthesic, vaso constrictors and spreading factors for plastic surgery treatments are known. See Fundamentals of Aesthetic Plastic Surgery, Stephen A. Sohn, published by Williamson & Wilkins, Pages 16-17. Such combinations have been employed in various dermabrasion procedure involving rotating abrasive wheels, surgical knives and scrapers to inhibit dermabrasion pain and blood-letting which interfers with the dermabrasion process.

The present method rapidly and effectively abrades selected portions of skin from a selected region. The combination of subcutaneous tissue treatment as described herein with selective ultrasonic surgical epidermis removal results in a rapid and effective reduction of skin wrinkles.

We claim:

1. A method for removing skin wrinkles from a region of living mammal skin, said skin wrinkles including raised portions of the epithelial layer which are elevated above a normal surface of said skin, by use of a high frequency vibrating tool having an output tip which comprises:
   a. introducing subcutaneously in said region (1) an effective amount of anesthetic; (2) an effective amount of vasoconstrictor; (3) an effective amount of enzyme spreading factor;
   b. selecting engaging said raised portions of the epithelial layer of said skin in said region with the output tip of said high frequency vibrating tool oscillating at frequencies from 20,000 to 50,000 Hertz to abrade selectively said raised portions of the epithelial skin layer in said region and to expose the subepithelial layer beneath said raised portions;
   c. allowing the exposed subepithelial skin layers to heal, whereby the region of skin has reduced skin surface irregularities.

2. The method of claim 1 in which the anaesthetic is lidocaine.

3. The method of claim 1 in which the vasonconstrictor is epinephrine.

4. The method of claim 1 in which the enzyme spreading factor is hyaluronidase.

5. The method of claim 1 in which the said high frequency vibrating tool has a power input of 35 to 50 watts.

* * * * *